| United States Patent [19] | [11] 4,063,923 |
|---|---|
| Han | [45] Dec. 20, 1977 |

[54] CARBAMOYLPHOSPHONIC ACID BRUSH CONTROL AGENTS

[75] Inventor: Jerry C-Y Han, Wilmington, Del.

[73] Assignee: E. I. Du Pont de Nemours and Company, Wilmington, Del.

[21] Appl. No.: 667,955

[22] Filed: Mar. 18, 1976

Related U.S. Application Data

[63] Continuation of Ser. No. 381,621, July 23, 1973, abandoned.

[51] Int. Cl.$^2$ .......................... A01N 9/36; C07F 9/38; C07F 3/06; C07F 13/01
[52] U.S. Cl. .................................. 71/86; 260/429 R; 260/429.9; 260/501.12; 260/502.5
[58] Field of Search .................. 260/502.5, 429, 429.9, 260/501.12; 71/86

[56] References Cited

U.S. PATENT DOCUMENTS

| 2,635,112 | 4/1953 | Fields | 260/502.5 |
|---|---|---|---|
| 3,223,514 | 12/1965 | Gradsten | 260/502.5 |
| 3,455,675 | 7/1969 | Irani | 260/502.5 |
| 3,627,507 | 12/1971 | Langsdorf | 260/924 |

Primary Examiner—Joseph E. Evans

[57] ABSTRACT

Carbamoylphosphonates such as monoammonium hydrogen carbamoylphosphonate are useful for regulation of the growth rate of plants.

9 Claims, No Drawings

CARBAMOYLPHOSPHONIC ACID BRUSH CONTROL AGENTS

This is a continuation of application Ser. No. 381,621, filed July 23, 1973, and now abandoned.

BACKGROUND OF THE INVENTION

This invention relates to novel carbamoylphosphonates and their use as brush control agents. The use of various carbamoylphosphonates for control of plant growth is known in the art. For example, U.S. Pat. No. 3,627,507 and Offenlegungsschrift No. 2,040,367 relate to the use of carbamoylphosphonates for plant growth control. However, neither of these references disclose the compounds of this case, nor do the references disclose a procedure by which the compounds of this invention can be made.

SUMMARY OF THE INVENTION

Compounds of the formula

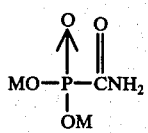

wherein
M is hydrogen, sodium, lithium, potassium, calcium, magnesium, zinc, manganese, barium or

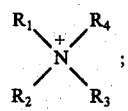

$R_1$ is hydrogen, alkyl of 1 to 4 carbon atoms or hydroxyalkyl of 2 to 4 carbon atoms;
$R_2$ is hydrogen, alkyl of 1 or 4 carbon atoms or hydroxyalkyl of 2 to 4 carbon atoms;
$R_3$ is hydrogen, alkyl of 1 to 4 carbon atoms or hydroxyalkyl of 2 to 4 carbon atoms; and
$R_4$ is hydrogen or alkyl of 1 to 12 carbon atoms;
provided that both M's are not hydrogen and that the total number of carbon atoms in $R_1$, $R_2$, $R_3$ and $R_4$ is less than 16, are useful as plant growth regulants. These compounds are particularly useful for retarding the growth of woody plants. These compounds can be applied to plants by directly contacting the plants with the compounds, or by applying the compounds to the soil in which the plants grow. Both of these modes of application are encompassed within the term "applying to plants" as used herein.

DESCRIPTION OF THE PREFERRED EMBODIMENTS

The compounds of this invention are prepared by hydrolysis of alkyl carbamoylphosphonate salts in very dilute, slightly acidic aqueous solutions. Once a carbamoylphosphonate salt is obtained, additional cations can be added by use of ion exchange columns or by contacting the compound with the appropriate base of salt. It should be noted that the activity of the compounds of this invention resides in the carbamoylphosphonate anion. The exact identity of the cations with which it is associated is of little significance. The preparation of the compounds of this case is further illustrated by the following Examples.

EXAMPLE 1

A solution of 0.1 part of ammonium ethyl carbamoylphosphonate in 50,000 parts of distilled water (pH 6.5) was kept at 60° C for one week. The water was then removed by vacuum distillation to give 0.08 part of the ammonium hydrogen carbamoylphosphonate. The product was characterized by TLC-electrophoresis which showed a doubly charged species at pH 10. The NMR showed no ethyl protons, while the IR gave a carbamoyl carbonyl peak at 1650 cm$^{-1}$.

In a similar way, the following compounds can be prepared starting with the appropriate salt of the carbamoylphosphonate.

sodium hydrogen carbamoylphosphonate
lithium hydrogen carbamoylphosphonate
potassium hydrogen carbamoylphosphonate
calcium hydrogen carbamoylphosphonate
magnesium hydrogen carbamoylphosphonate
zinc hydrogen carbamolyphosphonate
manganese hydrogen carbamoylphosphonate
barium hydrogen carbamoylphosphonate
methylammonium hydrogen carbamoylphosphonate
butylammonium hydrogen carbamoylphosphonate
2-hydroxyethylammonium hydrogen carbamoylphosphonate
dodecylammonium hydrogen carbamoylphosphonate
dimethylammonium hydrogen carbamoylphosphonate
dibutylammonium hydrogen carbamoylphosphonate
dodecylmethylammonium hydrogen carbamoylphosphonate
(4-hydroxybutyl)methylammonium hydrogen carbamoylphosphonate
trimethylammonium hydrogen carbamoylphosphonate
butyldimethylammonium hydrogen carbamoylphosphonate
dodecyldiethylammonium hydrogen carbamoylphosphonate
tri(2-hydroxyethyl)ammonium hydrogen carbamoylphosphonate
tetramethylammonium hydrogen carbamoylphosphonate
dodecyltrimethylammonium hydrogen carbamoylphosphonate

EXAMPLE 2

To a solution of 1.4 parts of sodium hydrogen carbamoylphosphonate in 25 parts of water is added 0.7 part of concentrated ammonium hydroxide. The solvent is removed under vacuum to give the desired ammonium sodium carbamoylphosphonate.

In a similar manner, the following compounds can be prepared from the appropriate mono salt of carbamoylphosphonic acid and the appropriate base.

| Starting Compound | Base | Product |
|---|---|---|
| sodium hydrogen carbamoylphosphonate | sodium hydroxide | disodium carbamoylphosphonate |
| potassium hydrogen carbamoylphosphonate | methylammonium hydroxide | methylammonium potassium carbamoylphosphonate |
| lithium hydrogen carbamoylphosphonate | dodecylammonium | dodecylammonium lithium carbonyl- |

-continued

| Starting Compound | Base | Product |
|---|---|---|
| dimethylammonium hydrogen carbamoyl-phosphonate | hydroxide dimethylammonium hydroxide | phosphonate bis(dimethylammonium)carbamoyl-phosphonate |
| calcium hydrogen carbamoylphosphonate | dibutylammonium hydroxide | dibutylammonium calcium carbamoylphosphonate |
| trimethylammonium hydrogen carbamoyl-phosphonate | trimethylammonium hydroxide | bis(trimethylammonium)carbamoylphosphonate |
| magnesium hydrogen carbamoylphosphnoate | triethylammonium hydroxide | triethylammonium magnesium carbamoylphosphonate |
| zinc hydrogen carbamoylphosphonate | tetramethylammonium hydroxide | tetramethylammonium zinc carbamoyl-phosphonate |
| dodecyltrimethylammonium hydrogen carbamoylphosphonate | dodecyltrimethyl-ammoniumhydroxide | bis(dodecyltrimethylammonium)carbamoylphosphonate |
| manganese hydrogen carbamoyl-phosphonate | 2-hydroxyethylammonium hydroxide | 2-hydroxyethylammonium manganese carbamoylphosphonate |
| barium hydrogen carbamoylphospnonate | 4-hydroxybutylammonium hydroxide | 4-hydroxybutylammonium barium carbamoylphosphonate |

The compounds of the invention are useful for modifying the growth rate of plants. The compounds of this invention are particularly useful in retarding the growth of woody plants. Thus, the compounds of this invention can be applied in areas such as power line rights-of-way where low-growing and slow-growing vegetation is especially desirable.

In addition to their value as plant growth retardants, the compounds of this invention can also be used to control flowering, fruit set, and coloration on apples and other fruits. They are useful in controlling the growth and flowering of ornamental species such as chrysanthemum and azalea.

The compounds of this invention can also be used to prolong the dormancy of perennial plants, and thereby protect the unsprouted buds from frost damage. This can be especially important in the protection of flower buds, which in some years may sprout early and be killed by cold temperatures. Application to plants in the stage where the next year's buds are being initiated, or are developing, gives marked retardation of bud break the following spring and greatly reduced growth.

To illustrate the growth retardant activity of the compounds of this invention, the following data are presented. Ammonium hydrogen carboxyphosphonate was applied in a solvent with a wetting agent and a humectant to pots of privet (*Ligustrum sp.*), willow (*Salix sp.*), Forsythia (*Forsythia sp.*), Arbor Vitae (*Thuja sp.*), and apple (*Malus sp.*). The plants were maintained in a greenhouse. Plant response ratings were taken one week and for weeks after application.

The term plant growth retardant as used in this disclosure is to be understood to mean an agent which when applied to a plant or its environs will slow the growth of the plant without killing or causing extensive injury to said plant. This also includes a delaying response on but sprouting or prolonging of the dormancy period.

The compounds of this invention can be applied as foliar sprays or as soil applications to retard the growth rate of such plants or to affect flowering and fruit set.

Preferably, the compounds of this invention are applied as foliar or dormant wood sprays to the point of runoff although lower-volume application can also be effective.

The compounds of the invention are very versatile and may be applied at one of many different time periods to suit the convenience of the applicator. For example they may be applied in Spring a short time prior to the period when maximum plant growth is anticipated, to effect growth retardation. They may be applied later in the growing season just after trimming, to effect growth retardation. Or they may be applied when the year's growth has ceased (late Summer, Fall, or Winter) with the result that treated plants will remain dormant the following Spring, whereas untreated plants will sprout and grow. If flowering and fruit set are to be modified, the treatment is applied before, during, or shortly after flowering.

It will be recognized tht the application rate is dependent upon the species to be treated and the results desired. In general, rates of from 0.25 to 20 kilograms per

| Application Rate, | Privet | | Willow | | Forsythia | | Arbor Vitae | | Apple | |
|---|---|---|---|---|---|---|---|---|---|---|
| Kg./hectare | 1 wk | 4 wks | 1 wk | 4 wks | 1 wk | 4 wks | 1 wk | 4 wks | 1 wk | 4 wks |
| 2.2 | 0 | 9G | 0 | 9G8D | 0 | 9G | 0 | 0 | 0 | 10G |
| 1.1 | 0 | 10G | 0 | 9G7D | 0 | 10G | 0 | 0 | 0 | 10G 10P |
| 0.6 | 0 | 6G | 0 | 9G8D | 0 | 9G | 0 | 0 | 0 | 10G |

The plant response ratings (above) are composed of a number and a letter. The number describes the extent of the response and ranges from zero to ten with zero representing no response, and ten representing 100% response. The letter describes the type of the response, as follows:

D, defoliation
G, growth retarded
P, terminal bud injury
X, axillary stimulation hectare are used although higher or lower rates can achieve the desired effect in some instances.

Useful formulations of the compounds of this invention can be prepared in conventional ways. They include dusts, granules, pellets, solutions, suspensions, emulsions, wetting powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

|  | Percent by Weight | | |
| --- | --- | --- | --- |
|  | Active Ingredient | Diluent(s) | Surfactant(s) |
| Wettable Powders | 20–90 | 0–74 | 1–10 |
| Oil Suspensions and Emulsions | 5–50 | 40–95 | 0–15 |
| Aqueous Solutions | 10–50 | 50–90 | 0–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing. Likewise, high levels of oils or humectants can be incorporated either in the formulation or by tank-mixing.

Typical solid diluents are described in Watkins, et al., "Handbook of Insecticide Dust Diluents and Carriers," 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending, and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook," 4th. Edn., McGraw-Hill, N.Y. 1963, pp. 8–59ff.

For further information regarding the art of formulation, see for example:

H. M. Loux, U.S. Pat. No. 3,235,361, 41.
W. P. Langsdorf, U.S. Pat. No. 3,627,507, Dec. 14, 1971. col. 8, line 1 through col. 11, line 12 and Examples 60–65.
G. C. Klingman, "Weed Control as a Science", John Wiley & Sons, Inc., New York, 1961 pp. 81–96.
J. D. Fryer and S. A. Evans, "Weed Control Handbook", 5th Edn. Blackwell Scientific Publications, Oxford, 1968, pp. 101–103.

The following Examples further illustrate the formulation and application of the compounds of this invention.

EXAMPLE 3

| Wettable Powder | |
| --- | --- |
| ammonium hydrogen carbamoylphosphonate | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

Eight kilograms of this formulation are mixed in a sprayer fitted with an agitator with 500 liters of water containing 0.5% of a non-phytotoxic wetting agent. The mixture is sprayed from a helicopter to a one hectare area under an electric power line in which the brush and trees have been freshly trimmed. This treatment retards the growth of black willow (*Salix nigra*), black cherry (*Prunus serotina*), and many other woody species.

EXAMPLE 4

| Water Soluble Powder | |
| --- | --- |
| ammonium sodium carbamoylphosphonate | 95.0% |
| dioctyl sodium sulfosuccinate | 0.5% |
| sodium ligninsulfonate | 1.0% |
| synthetic fine silica | 3.5% |

The ingredients are blended and coarsely ground in a hammer mill so that only a few percent of the active exceeds 250 microns (U.S.S. No. 60 sieve) in size. When added to water with stirring, the coarse powder initially disperses and then the active ingredient dissolves so that no further stirring is needed during application.

Fifteen kilograms of this formulation are mixed with 600 liters of water and sprayed on a one hectare area of newly trimmed hedgerow in the Spring after the leaves have expanded. (The spray may be either directly on the plants or to the soil in which the plants grow). This treatment greatly reduces the growth of plants growing in the hedgerow, but does not seriously injure them. Thus the hedgerow is kept neat with a minimum of labor expended from trimming it.

EXAMPLE 5

| Oil Suspension | |
| --- | --- |
| disodium carbamoylphosphonate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

One part of this suspension is mixed with one part of water in a sprayer fitted with an agitator, and applied in the winter to the point of runoff on the bark of dormant woody plants under a power line. The treated plants remain dormant for an extremely long period of time, thus greatly reducing plant growth and also the labor required for pruning.

I claim:

1. A compound of the formula $$\text{MO}-\overset{\overset{O}{\uparrow}}{\underset{\underset{OM}{|}}{P}}-\overset{\overset{O}{\|}}{C}NH_2$$

wherein

M is hydrogen, sodium, lithium, potassium, calcium, magnesium, zinc, manganese, barium or $$\begin{array}{c} R_1 \diagdown \overset{+}{N} \diagup R_4 \\ R_2 \diagup \diagdown R_3 \end{array};$$

$R_1$ is hydrogen, alkyl of 1 to 4 carbon atoms or hydroxyalkyl of 2 to 4 carbon atoms;

$R_2$ is hydrogen, alkyl of 1 to 4 carbon atoms or hydroxyalkyl of 2 to 4 carbon atoms;

$R_3$ is hydrogen, alkyl of 1 to 4 carbon atoms or hydroxyalkyl of 2 to 4 carbon atoms; and $R_4$ is hydrogen or alkyl of 1 to 12 carbon atoms;

provided that both M's are not hydrogen and that the total number of carbon atoms in $R_1$, $R_2$, $R_3$ and $R_4$ is less than 16.

2. A compound of claim 1 wherein M is hydrogen, sodium, lithium, potassium or ammonium.

3. The compound of claim 1, ammonium hydrogen carbamoylphosphonate.

4. A plant growth regulant composition consisting essentially of an inert diluent and an effective amount of a compound of claim 1.

5. A composition of claim 4 wherein M is hydrogen, sodium, lithium, potassium or ammonium.

6. The composition of claim 4 wherein the compound is ammonium hydrogen carbamoylphosphonate.

7. A method of controlling the growth rate of plants consisting essentially of applying to the plant an effective amount of a compound of claim 1.

8. A method of controlling the growth rate of plants consisting essentially of applying to the plant an effective amount of a compound of claim 2.

9. A method of controlling the growth rate of plants consisting essentially of applying to the plant an effective amount of a compound of claim 3.

* * * * *